United States Patent [19]

Totten et al.

[11] Patent Number: 4,477,930
[45] Date of Patent: Oct. 23, 1984

[54] NATURAL TISSUE HEAT VALVE AND METHOD OF MAKING SAME

[75] Inventors: Robert P. Totten; Gail S. Totten, both of Denver, Colo.; Mary A. Wilson, San Jose, Calif.

[73] Assignee: Mitral Medical International, Inc., Wheat Ridge, Colo.

[21] Appl. No.: 425,553

[22] Filed: Sep. 28, 1982

[51] Int. Cl.³ .............................................. A61F 1/22
[52] U.S. Cl. ....................................................... 3/1.5
[58] Field of Search ...................................... 3/1.5, 1

[56] References Cited

U.S. PATENT DOCUMENTS

| | | | |
|---|---|---|---|
| 3,548,418 | 12/1970 | Angell et al. | 3/1.5 |
| 3,655,306 | 4/1972 | Ross et al. | 3/1.5 X |
| 3,739,402 | 6/1973 | Cooley et al. | 3/1.5 |
| 3,755,823 | 9/1973 | Hancock | 3/1.5 |
| 3,983,581 | 10/1976 | Angell et al. | 3/1.5 |
| 4,035,849 | 7/1977 | Angell et al. | 3/1.5 |
| 4,084,268 | 4/1978 | Ionesco et al. | 3/1.5 |
| 4,172,295 | 10/1979 | Batten | 3/1.5 |

*Primary Examiner*—Ronald L. Frinks
*Attorney, Agent, or Firm*—John E. Reilly

[57] ABSTRACT

A low profile natural tissue heart valve with a one-piece fabric covering is applied to a stent in a minimum number of steps so that virtually no seams are exposed. The one-piece covering serves also to enclose and mount the sewing ring to avoid separation from the stent. The procedure employed enables use of bovine pericardium united as a single piece to the exterior of the stent and fixed in position in such a way as to avoid prolapsing in use.

18 Claims, 10 Drawing Figures

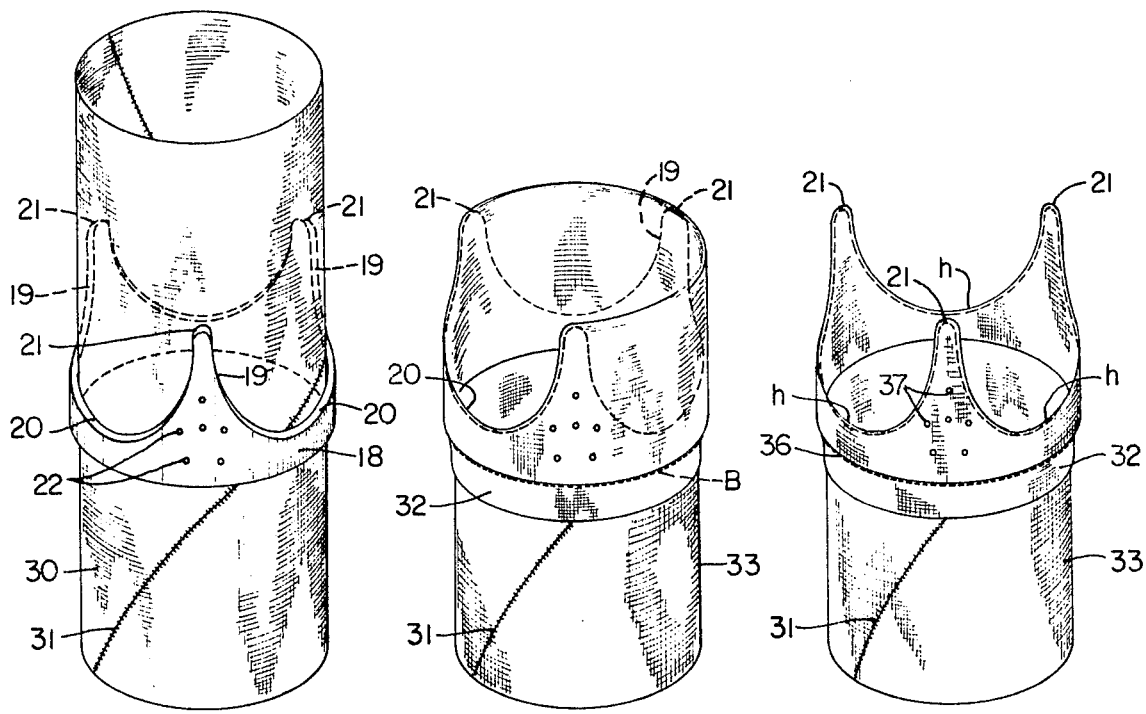
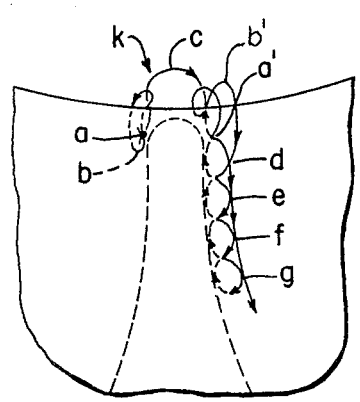
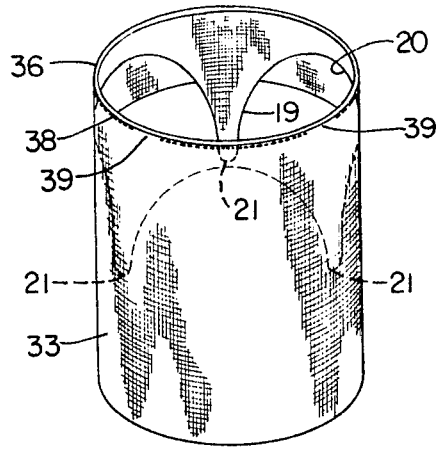

NATURAL TISSUE HEAT VALVE AND METHOD OF MAKING SAME

This invention relates to tissue valves; and more particularly relates to a novel and improved, low profile, natural tissue heart valve and to the method of making same.

BACKGROUND AND FIELD OF THE INVENTION

This invention is directed to certain improvements in the construction and method of fabrication of natural tissue heart valves of the type characterized by having a cloth or fabric covered stent which incorporates a suture ring at its base so as to facilitate its implantation into the annulus or wall of the heart using conventional surgical procedures. The valve element itself is composed of pericardium which is mounted upon and sewn to the stent and, for example, in a semicircular heart valve is so configured as to define three cusps which will undergo opening and closing in response to reversals in the flow of blood through the annulus.

In the construction of natural tissue heart valves, it is important that the valve have a low profile and specifically that the tissue valve support posts on the stent be as short as possible so as to avoid rupture of the ventricular wall. Low profile porcine valves have been devised but have not been found to possess the optimum hydrodynamic characteristics desirable in a tissue valve. Bovine pericardium has been employed in the past as the tissue valve for enhanced hydrodynamic performance but has been placed along the interior of the stent in order to effect the necessary support of the valve. A greater effective orifice area can be achieved if the bovine pericardium can be supported around the exterior of the stent and fabric covering while avoiding the necessity of making the stent unduly rigid or inflexible; and further if the necessary stitching or anchoring of the tissue or pericardium be performed between the tissue and exterior of the stent so that the leaflets can open as wide as possible while leaving a smooth interior thereby achieving a lower pressure drop. Thus, a closely-related consideration in the construction of the valve is that the stitching employed between the cloth covering, stent, sewing ring and tissue be uniform or symmetrical throughout and in such a way as to avoid the introduction of increased bulk or non-uniformities in thickness at any point as well as to eliminate any exposed seams or fabric edges. Achievement of the foregoing will then permit utilization of a single piece of tissue as the valve element which can be securely mounted in place onto the cloth-covered stent while maintaining a uniform internal diameter when the tissue valve element is expanded to its open position.

Previously, it has been the practice to employ pressure fixation in the pre-forming of the tissue valve element. However, it is desirable to avoid pressure fixation so as not to affect the collagen bundles in the tissue and in general to provide for an improved method of fixation of the tissue valve element with respect to the cloth-covered stent.

Representative patents of interest in the fabrication and construction of natural tissue heart valves are U.S. Pat. Nos. 3,548,418, 3,983,581 and 4,035,849 to W. W. Angell et al; 4,084,268 to M. I. Ionescu et al; and 4,172,295 to R. J. Batten.

SUMMARY OF THE INVENTION

Among the desirable objectives and advantages of the present invention in the construction of natural tissue heart valves is the formation of a low profile valve with a one-piece fabric covering applied to a stent in a minimum number of steps so that no raw seams or edges are exposed and wherein the one-piece covering will serve also to enclose and mount the sewing ring in place so as to avoid separation of the sewing ring from the stent. The procedure employed further enables the use of a pericardium or tissue which is united as a single piece element to the stent in such a way as not to prolapse in use.

In carrying out the teachings of the present invention, a single piece of fabric is formed into a tube which is sized for insertion within a circular mounting frame having a series of circumferentially spaced commissure posts, the latter separated by curved depressions or scalloped portions above a common annular base. One end of the tube is folded over the posts or tips leaving the longer portion of the tube inside of the stent. The folded-over portion of the tube is then stitched in closely surrounding relation to the posts and intervening scallops, after which the excess material is trimmed and the tubular portions inverted or turned inside out so as to place the seam inside of the inner and outer tube portions. The stent is reinserted into the scalloped tubular portion between the skirts, and the skirts are sewn together along the lower edge of the base of the stent followed by anchor stitching the outer skirt portion through sewing holes formed at spaced intervals within the body of each post. The remaining lengths of the skirt portions extending beyond the base stitching are then drawn over the outside of the stent and stitched together along a second base line of the skirt. An elastomeric sewing ring is inserted between the skirts so as to rest against the second base line and the longer skirt folded over the sewing ring and secured to the stent followed by stitching the short skirt to the long skirt.

The pericardium is specially selected and formed into a rectangular section of uniform thickness which is cut from a partially fixed pericardial sac. The rectangular section is secured to the base of the stent directly above the sewing ring with the fibrous outer layer of pericardium oriented to the inflow aspect or direction and with the abutting edges of the rectangular section located midway along one of the commissure posts. A continuous suture line is employed to secure the edge of the rectangular section to the base of the stent covering with knots formed at each of the commissure posts which are then hidden in pockets formed at the time of stent covering. A continous criss-cross suture line is then formed along each of the posts to secure the tissue thereto while leaving equal amounts of tissue in the depressions or scalloped portions between each of the posts for the formation of the cusps. Fixation of the tissue is carried out with the valves placed on a leaflet form mandrel and immersing in a bath of tissue fixative after which any final trimming is carried out.

Other objects, advantages and features of the present invention will become more readily appreciated and understood when taken together with the following detailed description in conjunction with the accompanying drawings, in which:

BRIEF DESCRIPTION OF THE DRAWINGS

FIG. 1 is a somewhat isometric view illustrating the first step in the fabrication of a natural tissue heart valve in which a fabric tube is inserted within a circular stent or frame;

FIG. 2 is an isometric view illustrating the seam which is formed between the fabric tube and scalloped edge of the stent;

FIG. 3 is an isometric view showing the folded-over portions of the tube inverted so as to place the seam along the scalloped edges inside followed by anchor stitching of the tube to the base of the stent;

FIG. 4 is an enlarged fragmentary view illustrating the stitching of the fabric to a post;

FIG. 5 is an isometric view with the stent inverted and showing the stitching of a second base line between the outer skirt portion of the tube and the base of the stent;

DETAILED DESCRIPTION OF THE PREFERRED EMBODIMENT

Figure 9:
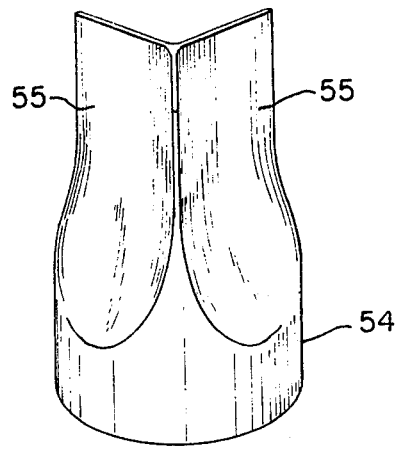
FIG. 9 is an isometric view in elevation of the forming tool employed in the mounting of the tissue into the desired configuration with respect to the stent.
Figure 10:
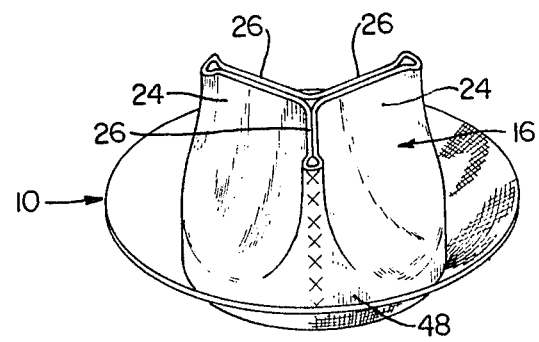
FIG. 10 is an isometric view of a preferred form of natural tissue valve formed in accordance with the present invention.

Referring in more detail to the drawings, there is illustrated in FIGS. 1 to 10 a preferred form of heart valve 10 which is broadly comprised of a stent 12, fabric covering 14 and pericardial tissue valve element 16. As shown in FIG. 1, the stent 12 is made up of an annular base 18 with three circumferentially spaced commissure posts 19 which project in a common direction at equally spaced circumferential intervals from the base and are separated by scallops or curved depressions 20. Preferably, the stent is composed of a plastic material possessing limited resiliency such that the commissure posts 19 are capable of undergoing inward and outward flexing in following the movement of the tissue valve element between the open and closed positions. Requisites of the material employed therefore are that it possess such limited resiliency and is not susceptible to creep. For instance, the stent may be molded from a polypropylene, ultra high density polyethylene, acetyl homo or copolymer materials. When laid out in a flat pattern, depressed areas 20 are of generally elliptical configuration with opposite side edges of the posts diverging away from tips 21 into the depressed areas. A plurality of apertures or sewing holes 22 are formed at spaced intervals to serve as one means of anchoring the fabric covering to the posts in a manner to be hereinafter described. For the purpose of reference, the upstream edge of the completed valve is located at the inflow end or base of the stent while the downstream or outflow end is along the posts 19; and in this relation the stent is arranged with the posts extending in the downstream direction to support the natural tissue element 16 in outer surrounding relation to the posts, the valve element 16 being pre-formed with three cusps 24 as shown in FIG. 10. As noted from FIG. 10, in the relaxed state the cusps are closed together along their downstream edges 26. However, in response to the flow of blood through the annulus the cusps will expand substantially beyond the full diameter of the stent 12, then under reversal in the flow of blood will return to their relaxed or closed state.

A sewing ring 28 is positioned in outer surrounding relation to the base of the stent and in a manner to be described is integrated into the valve by the fabric covering so as to serve as a secure means of implantation. The ring 28 may be composed of cloth, e.g., felt or a compliant elastomer, e.g., silicone elastomer which, upon grafting or implantation, will together with the covering 14, form a suitable base for fibrous ingrowth; also, the ring is sufficiently pliable as to conform to irregular openings but will assure a snug fit and seal with the wall of the annulus to which it is secured.

In the fabrication of the preferred form of tissue valve, the sequence of steps followed is illustrated in FIGS. 1 to 9 in accordance with the present invention. As illustrated in FIG. 1, a strip of bias cut fabric in the form of a parallelogram is configured into a tube 30 by sewing the raw edges together to form a bias seam 31 and the tube then inserted in close fitting relation within the stent 12 with the longer portion of the tube extending downwardly beyond the base of the stent. As seen from FIG. 2, the upper portion of the tube 30 is folded over the stent and overlaps the lower portion of the tube for a limited distance beyond the base so as to result in a relatively short skirt portion 32 and a longer skirt portion 33 on opposite sides of the stent. The skirt portions are basted together as at B along a circumferential line extending directly beneath the lower edge of the stent with the upper tip portions 21 of the commissure post 19 bearing snugly against the folded edge of the fabric tube. The fabric layers are then stitched along the posts 19 and scalloped edges 20 according to the procedure illustrated in FIGS. 3 and 4 wherein lock knots k are formed on opposite sides of each tip, then drawn together so as to snugly embrace opposite sides of each tip 21. Specifically, each lock knot k is formed by passing the thread through the fabric layers on one side of the tip as at point a and looping the suture or thread back over the frontal surface of the tip and returning it through the fabric layers at point b directly beneath point a and then advancing through the loop formed between a and b and continuing as at c over to the opposite side of the tip. The procedure is repeated on the opposite side of the tip where the thread enters the fabric layers at point a' is looped around through and into point b', then passed through the loop formed as at c' followed by drawing the suture together until the knots are tightly drawn against opposite sides of the tip with the threading c passing over the upper terminal edge of the tip.

After a pair of lock knots k have been formed on opposite sides of a tip, the remaining length of thread c' is then passed through a succession of back stitches as designated at d, e, f and g, this procedure being repeated throughout the length of the scalloped portion until the next commissure post is reached. Again, at the next commissure post, lock knots k are formed on opposite sides of the tip in the same manner as hereinbefore described. After the stitching operation is completed along the posts 19 and scalloped portions 20, the excess fabric along the scalloped portions and posts is trimmed as represented at h directly outside of the seam.

As a preliminary to the next fabrication step, the basting B is removed so as to permit removal of the stent from the folded end of the tube and permit the folded end to be inverted, or turned inside out, so that the seam formed along the scalloped portion is hidden or directed inwardly between the folds of the fabric. As illustrated in FIG. 3, once inverted, the stent is reinserted into the inverted end with the shorter skirt portion 32 again extending over the stent and the longer skirt portion extending within and beyond the stent notwithstanding that the folded end has been inverted. The stent is snugly inserted into the seamed or folded end of the fabric so as to be properly aligned with the lock knots snugly engaging opposite sides of each tip, following which the skirt portions are permanently stitched together along a circumferential base line 36 directly beneath the lower edge of the stent. Anchor stitching as represented at 37 is performed by passing the thread through the fabric layers and sewing holes 22 in each post, or in other words, passing the thread back and forth between the series of sewing holes so as to anchor opposite sides of the fabric covering securely to each post.

In a second base stitching operation, as illustrated in FIG. 5, the skirt portions 32 and 33 are reversed or pulled over the first base stitching 36 and with the stent inverted as shown in FIG. 5 both will be directed downwardly over the exterior of the stent and the fabric covering. The skirt portions then are permanently fixed together and to the outer fabric covering on the stent along a second circumferential base line 38. In this stitching procedure, with a lock knot 1 and back stitching over one rib of the fabric followed by sliding under three ribs of the fabric, stitching is continued along the circumferential line until the first post is reached, at which point a pocket 39 is form by leaving an area unstitched by a lock knot k, then sliding the needle for a limited distance to the opposite side of the post, forming another lock knot k and proceeding until the entire base has been stitched along the second base line 38.

Figure 6:
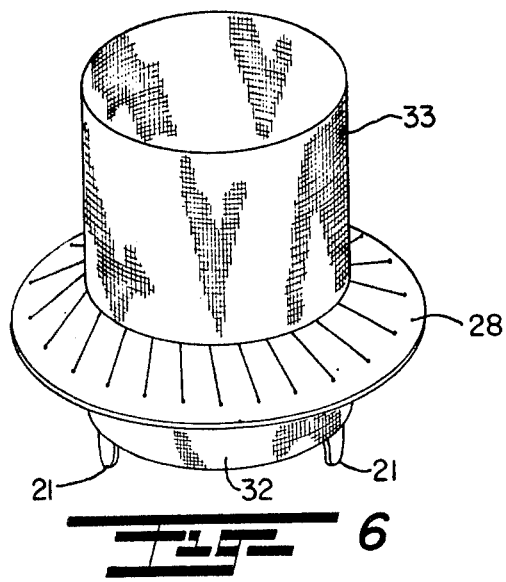
FIG. 6 is a view illustrating the first step in the anchoring of the sewing ring to the base of the stent.
Figure 7:
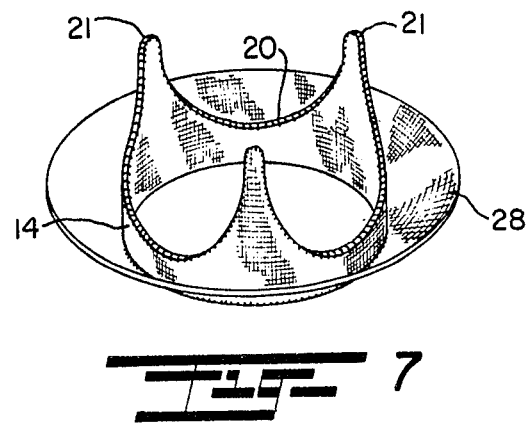
FIG. 7 is an isometric view of the completed fabric covering and stent.
Figure 8:
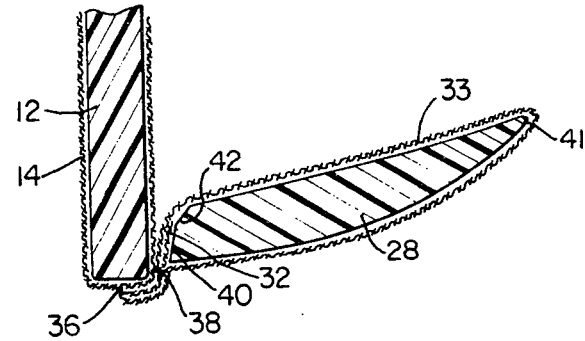
FIG. 8 is an enlarged cross-sectional view illustrating in more detail the anchoring of the sewing ring in place through the stent and skirt portions of the tube.

FIGS. 6 and 7 illustrate the placement of the sewing ring 28 at the base of the stent. By reference to FIG. 7, it will be noted that the sewing ring 28 is of annular configuration and in cross-section tapers from a flat inner edge 40 outwardly to a somewhat pointed extremity 41. In addition, to encourage the ring to lay smoothly when the skirt portions are pulled over it in a manner to be described and so as to be angled somewhat upwardly toward the post end of the stent, a corner 42 is trimmed off of the inner edge so as to form a beveled edge along the upper corner of the flat surface portion 40. The sewing ring is inserted between the skirt portions 32 and 33 with the bottom corner of the ring resting against the second base stitch 38 and the trimmed or upper corner 42 facing the posts 19 of the stent. The longer skirt portion 33 is of a length to be wrapped over the entire ring and with its terminal edge overlapping the shorter skirt portion 32 so that the skirt portions may be stitched together immediately above the second base line 38. As a preliminary to this stitching operation, and as best seen from FIG. 7, any excess fabric on the longer skirt 33 is trimmed to overlap the short skirt 32, and the skirt portions are closed together with a running stitch which connects the skirt 33 with the fabric covering over the stent except at the pocket areas 39, at which points the longer skirt portion is stitched to the shorter skirt 32.

FIG. 10 illustrates the mounting and integration of the tissue valve element 16 into the stent and fabric cover. As a preliminary to describing those steps, the preferred form of tissue valve element is a rectangular section of pericardium of uniform thickness which is cut from a partially fixed pericardial sac. The partial fixation is performed in a bath of tissue fixative, such as, a glutaraldehyde solution. This is the only period before the final fixation during which the tissue will contact the fixative. In accordance with conventional practice, the fibrous outer surface of the pericardium must be clear of fat and excess tissue. The rectangular section of pericardium is attached to the stent, as illustrated in FIG. 10, with the fibrous outer surface oriented to the inflow aspect. The tissue is first attached to the stent directly above the sewing ring 28 with the abutting edges of the tissue rectangle placed midway of one of the three commissure posts 19, the abutting edge portion being designated at 48. In order to secure the tissue to the fabric covering over the stent above the sewing ring 28, a continuous suture line is employed and which is tied off at each of the three commissure posts 19 with knots drawn into the pockets 39 left at the bases of the commissure posts 19 at the time of stent covering.

As best seen from FIG. 10, attachment of the tissue at each commissure post 19 is accomplished with a continuous criss-cross suture line 50. All three commissures are attached in this manner with care being taken to insure equal amounts of tissue being left for the formation of each cusp 24. Most of the excess free margin tissue above the posts is trimmed prior to fixation. FIG. 9 illustrates a leaflet type form mandrel 54 which is inserted through the stent and tissue valve element 16 with the hollowed-out portions 55 of the form mandrel aligned with the cusp portions 24 to be formed between the posts 19; i.e., along the scalloped portions 20. Fixation of the tissue is then carried out with the valve placed on the mandrel and immersed in a bath of tissue fixative, such as, a glutaraldehyde solution, for a period on the order of fourteen days. Application of mechanical pressure to the valve is avoided in the fixation of the valve so as to prevent distortion of the collagen bundles. Thus, it has been found that application of pressure to the tissue can be deleterious to the natural functioning of the collagen bundles so as to most closely simulate the human valve in operation. After fixation, the valve is given a final trim of excess tissue directly above the tips 21 of the posts so as to result in the completed valve as illustrated in FIG. 10.

The preferred form of tissue valve as illustrated finds equal utility for placement either in the atrioventricular valves; i.e., as a mitral or tricuspid valve; or as the aortic or pulmonary valve. Conventional surgical procedures are followed in the implantation of the valve and specifically by securing the outer sewing ring to the annulus or wall such that the cusps 24 on the valve are aligned in a downstream direction and will freely open to the maximum diameter of the stent under the opening pressure of the blood. When the pressure is reversed, the cusps will automatically close to their original state so as to operate effectively as a check valve. From the foregoing, it will be evident that the procedure followed in the fabrication and construction of the valve achieves a number of important advantages in the art of tissue valves, most notable of which are the utilization of a single piece of fabric for covering the stent and sewing ring followed by the use of a single section of tissue which can be securely fastened and united with the stent and fabric covering. In the resultant valve, no seams or knots are exposed so as to minimize any tendency to cause increased turbulence or interference in the blood flow and to simulate as close as possible the working of a natural human valve for the heart.

Preferably, a tissue valve is bovine pericardium having a thickness related to the external diameter of the stent and as indicated is selected so as not to have any blood vessels or excess fat. The tissue is formed into a rectangular piece which along the section covering the base is of a length corresponding to the outer circumference of the base of the covered stent so as to be able to be laid down into the pocket between the sewing ring 28 and stent 12. However, at the tip of the stent, the tissue is of increased length so as to be somewhat crown-shaped or of frusto-conical configuration toward the upper end or tips 21 of the stent. As described, the tissue is secured only to the external surfaces of the commissure posts 19 so as to be free to open fully to a diameter externally of the stent. Again, fixation is not performed until the tissue has been secured and trimmed, then is permitted to be fixed into the desired configuration without the application of pressure followed by sterilization and packaging in accordance with well-known practice.

It is therefore to be understood that the foregoing description of the construction of a natural tissue heart valve and method of making same is intended as a description of a preferred embodiment only and that various modifications, changes may be made in the construction and method of fabrication with out departing from the spirit and scope of the present invention as defined by the appended claims.

We claim:

1. In a prosthetic heart valve wherein an annular stent having a base at an upstream end and upright posts at spaced circumferential intervals around the downstream end of said stent, the improvement comprising:
    a one-piece fabric cover in the form of a tube having inner and outer concentric folds with said stent inserted between said folds such that said posts are disposed at the juncture of said folds, a first inverted seam in said fabric cover along said downstream end of said stent, and a base seam joining said folds circumferentially along said upstream end;
    a suture ring anchored to said base; and
    a tissue valve member circumscribing said stent and said outer fold.

2. In a prosthetic heart valve according to claim 1, said fabric cover defined by a bias cut fabric.

3. In a prosthetic heart valve according to claim 1, said inverted seam having knots positioned in snug-fitting engagement with opposite side edges of each of said posts.

4. In a prosthetic heart valve according to claim 1, said inverted seam defined by a continuous length of thread looped upon itself to define lock knots on opposite side edges of each post.

5. In a prosthetic heart valve according to claim 1, said fabric cover having inner and outer skirt portions extending from said base seam, and said suture ring anchored between said inner and outer skirt portions.

6. In a prosthetic heart valve according to claim 5, said skirt portions folded over said outer fold of fabric along the base of said stent, and a second base seam joining said skirt portions to said outer fold in closely spaced relation to said base seam.

7. In a prosthetic heart valve according to claim 6, one of said skirt portions folded over said suture ring and having a circumferential seam joining said one skirt portion to said outer fold adjacent to said second base seam.

8. In a prosthetic heart valve according to claim 1, said suture ring inclining outwardly away from said base in a direction toward said posts.

9. A prosthetic heart valve comprising:
    an annular stent having a base at an upstream end and upright posts at spaced circumferential intervals along a downstream end of said stent;
    a one-piece fabric cover in the form of a tube having inner and outer concentric folds between which said stent is inserted such that said posts are disposed at the juncture of said folds, a first inverted seam in said fabric cover along said downstream end of said stent, and a base seam joining said folds circumferentially along said upstream end;
    a suture ring anchored to said base; and
    a tissue valve element of tubular configuration disposed in surrounding relation to said stent, said element having mating edges extending midway of one of said posts and in a direction parallel to the direction of extension of said one post, one end of said element being anchored to the base of said stent in surrounding relation to said outer fold, and sutures extending in criss-cross relation through said valve element to anchor said valve element to each of said posts.

10. A prosthetic heart valve according to claim 9, said fabric cover defined by a bias cut fabric, and said inverted seam having knots positioned in snug-fitting engagement with opposite side edges of each of said posts.

11. A prosthetic heart valve according to claim 9, said inverted seam defined by a continuous length of thread looped upon itself to define lock knots on opposite side edges of each post.

12. A prosthetic heart valve according to claim 9, said fabric cover having inner and outer skirt portions extending from said base seam, said suture ring anchored between said inner and outer skirt portions, and said skirt portions being folded over said outer fold along the base of said stent, and a second base seam joining said skirt portions to said outer fold in closely spaced relation to said base seam and at the inner edge of said suture ring.

13. A prosthetic heart valve according to claim 12, one of said skirt portions folded over said suture ring and having a circumferential seam joining said one skirt portion to said outer fold adjacent to said second base seam.

14. A prosthetic heart valve according to claim 12, said second base seam having pockets at spaced intervals aligned with said posts for insertion of knots formed along the inner edge of said suture ring.

15. The method of forming a prosthetic heart valve, comprising the steps of:
    forming a tubular fabric cover;
    placing a stent having commissure posts over said tubular cover;
    reverse folding one end of said tubular cover over said stent whereby to define inner and outer concentric folds along inner and outer surfaces of said stent;
    forming a seam between said inner and outer folds along the downstream edge of said stent;

removing said stent from said tubular portion and inverting said tubular portion to place said seam inside of said inner and outer folds;

reinserting said stent into position between said inner and outer folds;

stitching a base seam in a circumferential direction between said inner and outer folds and beneath the upstream edge of said stent whereby to form inner and outer skirt portions in said fabric covering which extend away from said stent and said base seam;

reverse folding said inner and outer skirt portions over said stent;

inserting a suture ring between said inner and outer skirt portions; and folding one of said skirt portions over said suture ring and said other skirt portion and stitching said one skirt portion in a circumferential direction whereby to anchor said suture ring to said base.

16. The method according to claim 15, including the step of positioning a tissue valve element in surrounding relation to said outer fold and said stent with one edge of said valve element abutting said suture ring and the opposite edge of said valve element extending beyond the downstream edges of said stent and anchoring said tissue valve element in place to said fabric cover.

17. The method according to claim 15, characterized in that the seam formed along the downstream edge includes lock knots on opposite side edges of said posts.

18. The method of forming a tissue valve, comprising the steps of:

forming a tubular, bias cut fabric cover;

placing a stent over said tubular portion medially of the length of said tubular portion;

reverse folding one end of said tubular portion over said stent whereby to define inner and outer concentric folds along the inner and outer surfaces of said stent;

forming a seam between said inner and outer folds along the downstream edge of said stent;

removing said stent from said tubular portion and inverting said tubular portion to place said seam inside of said inner and outer folds;

reinserting said stent into position between said inner and outer folds;

stitching a base seam in a circumferential direction between said inner and outer folds and beneath the upstream edge of said stent whereby to form inner and outer skirt portions in said fabric covering which extend away from said stent and said base seam;

reverse folding said inner and outer skirt portions over said stent;

stitching a second base seam in a circumferential direction closely spaced to said first base seam between said skirt portions and said outer fold along the base of said stent;

inserting a suture ring between said inner and outer skirt portions into abutment with said second base seam;

folding one of said skirt portions over said suture ring and said other skirt portion and stitching said one skirt portion in a circumferential direction adjacent to said second base seam whereby to anchor said suture ring to said base; and positioning a tissue valve element in surrounding relation to said outer fold and said stent with one edge of said valve element abutting said suture ring and the opposite edge of said valve element extending beyond the downstream edges of said stent and anchoring said tissue valve element in place externally of said fabric cover.

* * * * *

UNITED STATES PATENT AND TRADEMARK OFFICE
CERTIFICATE OF CORRECTION

PATENT NO. : 4,477,930
DATED : October 23, 1984
INVENTOR(S) : Robert P. Totten, Gail S. Totten & Mary A. Wilson It is certified that error appears in the above-identified patent and that said Letters Patent is hereby corrected as shown below:

On the Title Page:

In the listing of the title, delete "Heat" and substitute -- Heart --.

In the Specification:

Column 1, line 2, delete "Heat" and substitute -- Heart --.
Column 5, line 36, delete "form" and substitute -- formed --.

Signed and Sealed this

Twenty-fifth Day of June 1985

[SEAL]

Attest:

DONALD J. QUIGG

Attesting Officer   Acting Commissioner of Patents and Trademarks